United States Patent [19]

Temperilli et al.

[11] Patent Number: 4,801,588
[45] Date of Patent: Jan. 31, 1989

[54] TETRACYCLIC INDOLE DERIVATIVES FOR TREATING HYPERTENSION

[75] Inventors: Aldemio Temperilli, Milan; Rosanna Eccel, Cornate d'Adda; Enzo Brambilla, Mariano Comense; Patricia Salvati, Arese, all of Italy

[73] Assignee: Farmitalia Carlo Erba S.p.A., Milan, Italy

[21] Appl. No.: 73,438

[22] Filed: Jul. 15, 1987

[30] Foreign Application Priority Data

Jul. 22, 1986 [GB] United Kingdom ............... 8617907

[51] Int. Cl.$^4$ ............... A61K 31/40; A61K 31/415; C07D 487/02
[52] U.S. Cl. ............... 514/274; 514/389; 544/310; 548/309; 548/421
[58] Field of Search ............... 544/310; 514/274, 389; 548/421, 309

[56] References Cited

U.S. PATENT DOCUMENTS 4,317,912 3/1982 Temperilli et al. ............... 548/421
4,690,929 9/1987 Bernardi et al. ............... 546/69

OTHER PUBLICATIONS

Temperilli et al., Chemical Abst. 94-209049h.

Primary Examiner—Donald G. Daus
Assistant Examiner—Cecilia Shen
Attorney, Agent, or Firm—Oblon, Fisher, Spivak, McClelland & Maier

[57] ABSTRACT

Compounds of the formula I:

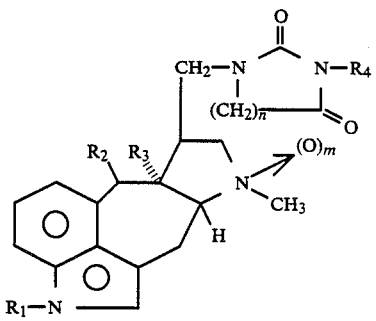

wherein $R_1=H$, $CH_3$; $m=0,1$; $R_2=R_3=H$ or $R_2$, $R_3=$bond, $R_4=C_1$–$C_4$ hydrocarbon, $n=1$ or 2 and their pharmaceutically acceptable salts are antihypertensive agents. Their preparation and pharmaceutical compositions containing them are also described.

11 Claims, No Drawings

TETRACYCLIC INDOLE DERIVATIVES FOR TREATING HYPERTENSION

FIELD OF THE INVENTION

The present invention relates to tetracyclic indole derivatives and to a process for their preparation.

SUMMARY OF THE INVENTION

The present invention provides novel 5(10→9)abeo-ergoline derivatives having the general formula I:

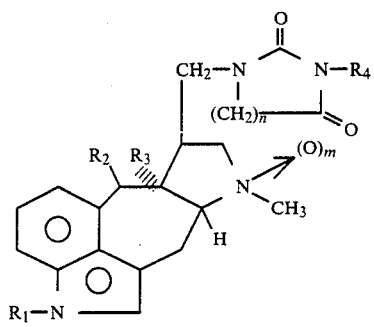

wherein $R_1$ represents a hydrogen atom or a methyl group, $R_2$ and $R_3$ represent each a hydrogen atom or taken together represent a chemical bond, $R_4$ represents a hydrogen atom or a hydrocarbon group having from 1 to 4 carbon atoms and n is 1 or 2 and m is 0 or 1.

Pharmaceutically acceptable salts of these ergoline derivatives are included in the invention.

DETAILED DESCRIPTION OF THE PREFERRED EMBODIMENTS

In the definition of $R_4$, a hydrocarbon group having from 1 to 4 carbon atoms is intended to include alkyl, cycloalkyl and unsaturated (both ethylenically and acetylenically) groups.

Representative moieties include methyl, ethyl, n-propyl, isopropyl, butyl, t-butyl, isobutyl, cyclopropyl, methlcyclopropyl, vinyl, allyl and propargyl.

Pharmaceutically acceptable salts refer to those salts which retain biological effectiveness and properties of the free bases and which are not biologically or otherwise undesirable, formed with inorganic acids such as hydrochloric, hydrobromic, sulfuric, nitric or phosphoric acid; and organic acids such as acetic, propionic, glycolic, pyruvic, oxalic, malic, malonic, succinic, maleic, fumaric, tartaric, citric, benzoic, cinnamic, mandelic, methanesulfonic, ethanesulfonic, p-toluene sulfonic or salicyclic acid.

The present invention also provides a process for the preparation of 5(10→9)abeo-ergoline derivatives of general formula I which comprises the step of condensing a 5(10→9)abeo-ergoline of the formula II

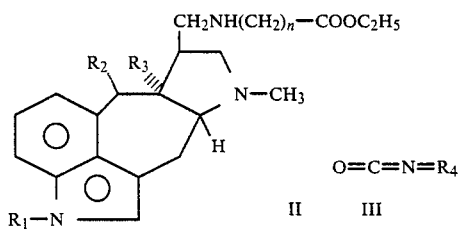

wherein $R_1$, $R_2$, $R_3$ and n are as above defined with a compound of formula III wherein $R_4$ is as above defined and the optional step of N-oxidizing the resultant cyclic compounds with organic peracids such as perbenzoic or monoperphthalic or m-chloroperbenzoic acid to give the compounds of formula I wherein m is 1. The condensation-cyclization process may be carried out in a solvent such as water or ethanol with addition of acid such as hydrochloric acid at a temperature of from 50° to 100° C. for 2 to 10 hours. The optional N oxidation process may be carried out in a solvent such as chloroform or tetrahydrofuran or dimethylformamide at a temperature of 0° to 25° C. for 2 hours. The 5(10→9)abeo-ergolines of the general formula II may be prepared by established procedures starting from known compounds.

According to one preferred method the compound of the general formula II wherein n is 1 may be obtained by reacting an appropriate 5(10→9)abeo-ergolinemethanamine with ethyl acrylate. Alteratively a compound of formula $Br(CH_2)_n COOC_2H_5$ wherein n is as above defined may be made to react with an appropriate 5(10→9)abeo-ergolinemethanamine in the presence of acid scavenger such as potassium carbonate to give the compounds of the general formula II. The compounds of formula III are known compounds and when $R_4 = H$ may be generated in situ by reaction of an appropriate salt thereof with an acid such as hydrochloric acid. Free base forms of the compounds of formula I may be converted into acid addition salt forms in conventional manner and vice versa.

The compounds of the present invention and their pharmaceutically acceptable salts are useful antihypertensive agents with a slow onset of action and long lasting activity.

EVALUATION OF ANTIHYPERTENSIVE ACTIVITY

Methods

Intrarterial measurements of mean blood pressure (MBP) were performed through catheters (PE 50, Clay Adams) implanted in the rat (SHR) right carotid artery under alothane anesthesia. Twenty four hours after surgery, the animals were placed in Ballman cages and the arterial cannula was connected via a pressure transducer to a Beckman blood pressure recorder for continuous monitoring of mean blood pressure.

MBP was recorded before the oral administration (basal values) and 15-30-60-120-240 minutes till 24 hours after treatment. Groups of 7-8 rats were orally treated with a single dose of the test compound or vehicle, methocel 0.5% w/v (0.2 ml/100 g b.w.). The $ED_{25}$ was calculated for each compound from the dose-response regression line.

As reference standard drug, captopril was also tested. The $ED_{25}$ (dose lowering mean blood pressure of 25 mmHg) obtained with the compounds under study are reported in table 1.

EVALUATION OF THE TOXICITY

Three male mice for each group were orally treated with drugs at different dose levels for the determination of orientative toxicity. Mice were observed for seven days after administration. The data ($DL_{50}$) obtained are summarized in Table I.

TABLE I

| Compound | LD$_{50}$ mg.kg$^{-1}$ p.o. | ED$_{25}$ and limits mg.kg$^{-1}$ p.o. P = 0.05 |
| --- | --- | --- |
| FCE 24379 Example 1b | >800 | 1.229 (0.661–1.845) |
| FCE 24778 Example 1c | >800 | 0.402 (0.297–0.511) |
| FCE 24378 Example 2a | >800 | 2.051 (1.180–2.971) |
| FCE 25068 Example 2b | >800 | 4.272 (3.256–5.514) |
| Captopril (standard drug) | >800 | 13.73 (7.86–23.04) |

The invention further comprises a pharmaceutical composition containing a therapeutically effective amount of a compound of formula I or a pharmaceutically acceptable salt thereof in admixture with a pharmaceutically acceptable diluent or carrier. The administration of compounds I and their non-toxic pharmaceutically acceptable acid addition salts or mixtures thereof may be achieved either parenterally or orally, preferably orally.

As used herein, the term "effective amount" encompasses those amounts which yield the desired activity without causing adverse side effects. However, an effective dosage is in the range of about 0.001 to 0.5 mg/Kg day, preferably 0.01 to 0.25 mg/Kg day.

The pharmaceutical carriers which are typcially employed with the compounds of the invention may be solid or liquid and are generally selected dependent on the planned manner of administration. Thus, for example, solid carriers include lactose, sucrose, gelatin and agar and the like, while liquid carriers include water, syrup, peanut oil and olive oil and the like.

The combination of the selected compound and the carrier may be fashioned into numerous acceptable forms such as tablets, capsules, suppositories, solutions, emulsion, powders and syrups.

The following Examples illustrate the invention without limiting it.

EXAMPLE 1

1[[5-(10→9)abeo-9,10-didehydro-6-methylergolin-8β-yl]methyl]-2,4-(1H,3H)-pyrimidinedione-N$_6$-oxide (a)

5-(10→9)abeo-9,10-didehydro-6-methyl-ergoline-8β-methanamine 10.3 g of triphenylphosphine, 5.4 g of phthalimide and 6.9 g of ethyl azodicarboxylate were added under stirring at 25° C. to a solution of 5 g of 5(10→9)abeo-9,10-dedehydro-6-methylergoline-8β-methanol in 100 ml of tetrahydrofuran. After 1 hour the solvent was evaporated off in vacuo and the residue was taken up in 10% tartaric acid. The solution was repeatedly extracted with ethyl acetate, then made basic with ammonium hydroxide and extracted with dichloromethane. Evaporation of the dichloromethane left a crude residue of 6.3 g of 2-[[5(10→9)abeo-9,10-didehydro-6-methylergolin-8β-yl]-methyl]-1H-isoindole-1,3(2H)-dione (m.p. 174°–176° C.). This was dissolved in 80 ml of ethanol and 80 ml of tetrahydrofuran, 3.15 ml of hydrazine hydrate were added and the solution was refluxed for 5 hours. After evaporation of the solvent the residue was taken up in water and dichloromethane. Evaporation of the organic layer left 4 g of the title compound (amorphous).

(b)

1-[[5-(10→9)abeo-9,10-didehydro-6-methylergolin-8β-yl]methyl]-2,4-(1H,3H)-pyrimidinedione A mixture of 3.25 of 5(10→9)abeo-9,10-didehydro-6-methylergoline-8β-methanamine and 1.45 ml of ethyl acrylate in 50 ml of ethanol was refluxed for six hours. The solvent was evaporated and the residue was chromatographed on a silica gel column using ethyl acetate with increasing amounts of ethanol (from 0 to 10 percent) as eluant to give 3.3 g of N-[[5-(10→9)abeo-9,10-didehydro-6-methylergolin-8β-yl]methyl]-β-alanine ethyl ester melting at 128°–130° C.

To a solution of 1.53 g of potassium cyanate in 15 ml of water a solution of 3.3 g of N-[[5-(10→9)abeo-9,10-didehydro-6-methylergolin-8β-yl]methyl]-β-alanine ethyl ester in 60 ml of water and 18.6 ml of 1N hydrochloric acid was added. The mixture was heated for nine hours at 90° C. then the solid that separated was filtered and purified by chromatography on silica gel column using dichloromethane with increasing amounts of methanol (from 0 to 8 percent) as eluant to give 2.1 g of the title compound melting at 234°–236° C.

(c)

1-[[5-(10→9)abeo-9,10-didehydro-6-methylergolin-8β-yl]methyl]-2,4-(1H,3H)-pyrimidinedione-N$_6$-oxide A solution of 1.37 g of 1-[[5-(10→9)abeo-9,10-didehydro-6-methylergoline-8β-yl]methyl]-2,4-(1H,3H)-pyrimidinedione in 80 ml of tetrahydrofuran and 10 ml of dimethylformamide was treated with 0.84 g of m-chloroperbenzoic acid in 10 ml of tetrahydrofuran. This solution was left at room temperature for one hour then the solvent was evaporated. Addition of 6 ml of water containing 0.42 g of sodium bicarbonate gave 1.1 g of the title compound which was recovered by filtration, m.p. 198°–200° C.

EXAMPLE 2

1[[5-(10→9)abeo-9,10-didehydro-6-methylergolin-8β-yl]methyl]-2,4-imidazolidinedione-N$_6$-oxide (a)

1-[[5(10→9)abeo-9,10-didehydro-6-methylergolin-8β-yl]methyl]-2,4-imidazolidinedione A solution of 1.93 ml of ethyl bromoacetate in 10 ml of dimethylformamide was added to a cooled suspension of 4.3 g of 5(10→9)abeo-9,10-didehydro-6-methylergolin-8β-methylamine and 2.4 g of potassium carbonate in 50 ml of dimethylformamide. When the reaction was over the solution was reduced in volume by evaporation in vacuo, poured into iced water and extracted with dichloromethane.

The residue of the organic layer was purified by column chromatography on silica gel using ethyl acetate with increasing amounts of ethanol (from 0 to 10 percent) as eluant, to give 3.5 g of N-[[5(10→9)abeo-9,10-didehydro-6-methylergolin-8β-yl]methyl]-glycine ethyl ester melting at 141°–142° C.

3.5 g of N-[[5(10→9)abeo-9,10-didehydro-6-methylergolin-8β-yl]methyl]-glycine ethyl ester were treated with 1.67 g of potassium cyanate, as described in Example 1b, and the title compound, m.p. 170°–172° C., was obtained in 75% yield.

(b) 1-[[5(10→9)abeo-9,10-didehydro-6-methylergolin-8β-yl]methyl]-2,4-imidazolidinedione-N6-oxide Operating as in Example 1c, but employing 1-[[5(10→9)abeo-9,10-didehydro-6-methylergolin-8β-yl]methyl]-2,4-imidazolidinedione, the title compound m.p. 218°-220° C., was obtained in 75% yield.

EXAMPLE 3

1-[[trans-5(10→9)abeo-1,6-dimethylergolin-8β-yl]methyl]2,4-(1H,3H)-pyrimidinedione Operating as in Example 1, but employing trans-5(10→9)abeo-1,6-dimethylergoline-8β-methanamine instead of 5(10→9)abeo-9,10-didehydro-6-methylergoline-8β-methanamine, the title compound, m.p. 185°-187° C., was obtained in 55% yield.

EXAMPLE 4

1-[[trans-5(10→9)abeo-1,6-dimethylergolin-8β-yl]methyl]2,4-(1H,3H)-pyrimidinedione-N6-oxide Operating as in Example 1, but employing 1-[[trans-5(10→9)abeo-1,6-dimethylergolin-8β-yl]methyl]2,4-(1H,3H)-pyrimidinedione, the title compound, m.p. 204°-206° C., was obtained in 83% yield.

EXAMPLE 5

1-[[trans-5(10→9)abeo-6-methylergolin-8β-yl]methyl]-2,4-imidazolidinedione

Operating as in Example 2, but employing trans-5(10→9)abeo-6-methylergoline-8β-methanamine obtained as in Example 1 starting from trans-5(10→9)abeo-6-methylergoline-8β-methanol, the title compound, m.p. 168°-170° C., was obtained in 55% yield.

EXAMPLE 6

1-[[trans-5(10→9)abeo-6-methylergolin-8β-yl]methyl]-2,4-imidazolidinedione-N6-oxide Operating as in Example 2, but employing 1-[[trans-5(10→9)abeo-6-methylergolin-8β-yl]methyl]-2,4-imidazolidinedione, the title compound, m.p. 187°-189° C., was obtained in 80% yield.

We claim:

1. A compound of the formula I:

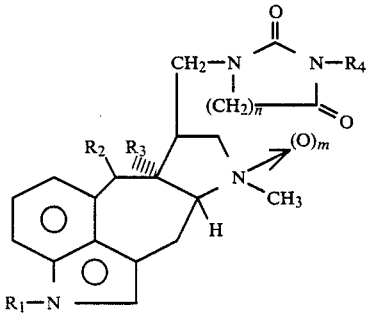

wherein $R_1$ represents a hydrogen atom or a methyl group, $R_2$ and $R_3$ represent each a hydrogen atom or, taken together, represent a chemical bond, $R_4$ represents a hydrogen atom or a $C_{1-4}$ alkyl group, a $C_{3-4}$ cycloalkyl group, an ethylenically unsaturated $C_{2-4}$ alkyl group, or an acetylenically unsaturated $C_{2-4}$ alkyl group, and n is 1 or 2, and m is 0 or 1, and a pharmaceutically acceptable salt thereof.

2. A compound of formula I according to claim 1 wherein $R_4$ represents hydrogen atom.

3. A compound according to claim 1 which is 1[[5(10→9)abeo-9,10-didehydro-6-methylergolin-8β-yl]methyl]-2,4,(1H,3H)-pyrimidinedione-N6-oxide.

4. A compound according to claim 1 which is 1[[5-(10→9)-abeo-9,10-didehydro-6-methylergolin-8β-yl]methyl]-2,4-(1H,3H)-pyrimidinedione.

5. A compound according to claim 1 which is:
1-[[5(10→9)abeo-9,10-didehydro-6-methylergolin-8β-yl]methyl]-2,4-imidazolidinedione;
1-[[5(10→9)abeo-9,10-didehydro-6-methylergolin-8β-yl]methyl]-2,4-imidazolidinedione-N6-oxide;
1-[trans-5(10→9)abeo-1,6-dimethylergolin-8β-yl]-methyl-2,4-(1H,3H)-pyrimidinedione;
1-[[trans-5(10→9)abeo-1,6-dimethylergolin-8β-yl]methyl]-2,4-(1H,3H)-pyrimidinedione-N6-oxide;
1-[[trans-5(10→9)abeo-6-methylergolin-8β-yl]methyl]-2,4-imidazolidinedione; or
1-[[trans-5(10→9)abeo-6-methylergolin-8β-yl]methyl]-2,4-imidazolidinedione-N6-oxide.

6. A pharmaceutical composition for treating hypertension comprising an effective amount of a compound of formula I according to claim 1 or a pharmaceutically acceptable salt thereof in admixture with a pharmaceutically acceptable diluent or carrier.

7. A method of treating hypertension in a patient in need thereof, comprising administering to said patient an amount effective for treatment of hypertension of a compound of formula I:

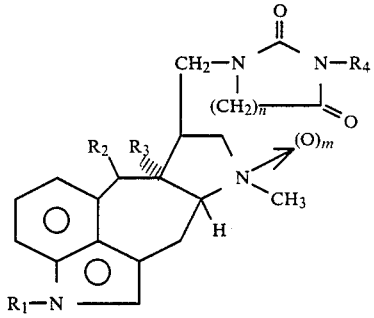

wherein:
$R_1$ represents a hydrogen atom or a methyl group;
$R_2$ and $R_3$ represent each a hydrogen atom or, taken together, represent a chemical bond;
$R_4$ represents a hydrogen atom, a $C_{1-4}$ alkyl group, a $C_{3-4}$ cycloalkyl group, an ethylenically unsaturated $C_{2-4}$ alkyl group, or an acetylenically unsaturated $C_{2-4}$ alkyl group; and
n is 1 or 2, m is 0 or 1, or a pharmaceutically acceptable salt thereof.

8. The method of claim 7, wherein $R_4$ is a hydrogen atom.

9. The method of claim 7, wherein said compound is 1-[[5(10→9)abeo-9,10-didehydro-6-methylergolin-8β-yl]-methyl]-2,4-(1H,3H)-pyrimidinedione-N6-oxide.

10. The method of claim 7, wherein said compound is 1-[[5(10→9)abeo-9,10-didehydro-6-methylergolin-8β-yl]-methyl]-2,4-(1H,3H)-pyrimidinedione.

11. The method of claim 7, wherein said compound is 1-[[5(10→9)abeo-9,10-didehydro-6-methylergolin-8β-yl]-methyl]-2,4-imidazolidinedione; 1-[[5(10→9)abeo- 9,10-didehydro-6methylergolin-8β-yl]-methyl]-2,4-imidazolidinedione-$N_6$-oxide; 1-[trans-5(10→9)abeo-1,6-dimethylergolin-8β-yl]methyl-2,4-(1H,3H)-pyrimidinedione; 1-[[trans-5(10→9)abeo-1,6-dimethylergolin-8β-yl]methyl]-2,4-(1H,3H)-pyrimidinedione-$N_6$-oxide; 1-[[trans-5(10→9)abeo-6-methylergolin-8β-yl]methyl]-2,4-imidazolidinedione; or 1-[[trans-5(10→9)abeo-6-methylergolin-8β-yl]methyl]-2,4-imidazolidinedione-$N_6$-oxide.

* * * * *